United States Patent [19]
Hess et al.

[11] Patent Number: 5,814,083
[45] Date of Patent: Sep. 29, 1998

[54] PACEMAKER TACHY DETERMINATION BASED BLOCKED ON 2:1 SENSING

[75] Inventors: Michael F. Hess, Minneapolis; H. Toby Markowitz, Roseville, both of Minn.

[73] Assignee: Medtronic, Inc, Minneapolis, Minn.

[21] Appl. No.: 536,597

[22] Filed: Sep. 29, 1995

[51] Int. Cl.$^6$ ............................................. A61N 1/365
[52] U.S. Cl. ................................................. 607/14
[58] Field of Search ............................... 607/9, 14

[56] References Cited

U.S. PATENT DOCUMENTS

| | | |
|---|---|---|
| 4,363,325 | 12/1982 | Roline . |
| 4,374,382 | 2/1983 | Markowitz . |
| 4,556,063 | 12/1985 | Thompson . |
| 4,562,841 | 1/1986 | Brockway . |
| 4,587,970 | 5/1986 | Holley . |
| 4,624,260 | 11/1986 | Baker, Jr. et al. ................. 607/14 |
| 4,712,556 | 12/1987 | Baker, Jr. ........................... 607/14 |
| 4,856,523 | 8/1989 | Sholder . |
| 4,856,524 | 8/1989 | Baker . |
| 5,052,388 | 10/1991 | Sivula . |
| 5,127,404 | 7/1992 | Wyborny . |
| 5,144,949 | 9/1992 | Olson . |
| 5,271,395 | 12/1993 | Wahlstrand . |
| 5,284,491 | 2/1994 | Sutton . |

OTHER PUBLICATIONS

Provenier et al., The "Automatic Mode Switch" Function in Successive Generations of Minute Ventilation Sensing Dual Chamber Rate Responsive Pacemakers, in Pace, vol. 17, Nov. 1994, Part II, pp. 1913–1919.

Ovsyshcher et al. "Initial Experience with a New Algorithm for Automatic Mode Switching from DDDR to DDIR Mode", Pace, vol. 17, Nov. 1994, Part II, pp. 1908–1912.

Levine, et al., A New Automode Switch Algorithm for Supraventricular Tachycardias, in Pace, vol. 17, Nov. 1991, Part II, pp. 1895–1899.

den Dulk et al., Initial Experience with Mode Switcing in a Dual Sensor, Dual Chamber Pacemaker in Patients with Paroxysmalatrial Tachyarrhythmias, in Pace, vol. 17, Nov. 1994, Part II, pp. 1990–1907.

*Primary Examiner*—William E. Kamm
*Assistant Examiner*—George R. Evanisko
*Attorney, Agent, or Firm*—Harold R. Patton; Michael B. Atlass

[57] ABSTRACT

Some false tachy detection prevention algorithms miss blocked 2:1 sensing and therefore miss some true tachy situations. Here an algorithm that uses sensed far field R waves to determine whether to search for blocked 2:1 sensing is implemented and a search algorithm is also described.

13 Claims, 6 Drawing Sheets

PACEMAKER TACHY DETERMINATION BASED BLOCKED ON 2:1 SENSING

BACKGROUND OF THE INVENTION

In general, this invention relates to implantable pulse generators used to deliver stimulation to pace a patient's heart and particularly to those which detect atrial tachycardia and switch to either an antitachy pacing mode or another mode (called mode switching) on discovering indications of atrial tachycardia or atrial tachyarrhythmias.

In response to such indications, a pacemaker may perform in a number of different ways and it is not the purpose of this invention to detail such responses. Rather this invention is designed to prevent or reduce false responses, and further, teaches how to avoid missing out on true determinations of tachyarrhythmias under circumstances where 2:1 sensing is possibly occurring.

One method of responding to indications of tachycardia generally ignores the high intrinsic atrial rates and switches to ventricular pacing as described in U.S. Pat. No. 5,144,949 (Olson). This is a type of mode switching. Other systems use alternative operations in antitachy mode such as that described in U.S. Pat. No. 4,587,970 (Holley et al.) which uses reversion pacing to try to disrupt and discontinue the tachycardia. A fairly detailed background on pacemaker technology for mode switching is found in U.S. Pat. No. 4,562,841 (Brockway et al.).

Mode switching has had various definitions and purposes in the pacemaker or pacing and pulse generator art. Examples, besides those mentioned above, include U.S. Pat. Nos. 5,284,491 (Sutton et al.), 4,856,523 (Sholder et al.), and 4,363,325 (Roline et al.). These use a sensor rate or some long term or changing atrial rate to determine when mode switching is to be done for the particular problems that those patents address. In general they are inventions responsive to problems developed because of or during rate adaptive pacing. Mode switching can best be described as where the pacemaker reverts to a mode that does not track (i.e., does not pace the ventricle in synchronization to) the atrial rate. Another way to say this is that in a mode switched condition ventricular pacing is not synchronized to intrinsic atrial activity.

Methods and features of mode switching are described in the Nov. 19, 1994 (Vol. 17, Part II) issue of PACE magazine in the article titled "A New Automode Switch Algorithm for Supraventricular Tachycardias" by Levine et al on pp.1895–9. (Additional articles on automatic mode switching devices were also published in the same issue of PACE at pages 1900(Den Dulk), 1908(Ovsyshcher) and 1913 (Provenier).

Rate adaptive pacers which follow a patient's physiologic demand have been available for some time. A recent example is illustrated in U.S. Pat. No. 5,271,395 (Wahlstrand et al.). U.S. Pat. No. 4,856,524 (Baker, Jr.) uses an AV interval timer instead of an activity sensor (as in U.S. Pat. No. 5,052,388 to Sivula et al.) or minute ventilation (as in U.S. Pat. No. 5,271,395 Wahlstrand) to determine the appropriate pacing rate.

Pacemaker technology has been around for some 30 years. The technology for implanting such hermetically sealed electrical pulse generators (usually with batteries for power) responsive to a patient's pacing needs are well known in many aspects and those will not be described with particularity here. Instead, the reader should refer to descriptions available in the art cited in this application and other readily available literature.

When the pacemaker is adapted to search for and respond to tachy conditions (i.e., mode switching) the presence of far field R-waves (FFRWs) cause false positive mode switching. (A FFRW is defined as atrial sensing of ventricular depolarization).

In responding to the problem of false positive tachy detection, the implantable pulse generator (PG) had often been pacing at or near the programmed lower rate before, during, and after the erroneous indicator caused a modeswitch. Commonly that response was referred to as a mode switch episode. These episode durations were generally short (less than one minute) and ends when FFRW sensing stops. The AP-VP-AR and AP-AR-VS timing sequences (where the AP-AR interval is long relative to the size of the interval AR-AP) sustained over multiple pacing cycles were generally felt responsible for false positive tachy detection and thus causing these mode switch episodes. (Definitions: AP=atrial pace, VP=ventricular pace, VS=ventricular sense, and AR=atrial refractory sense). Because a pacemaker senses these events through intracardiac electrical lead(s), it is thought that these patterns can be the result of far field R-wave sensing. Test results using marker channel information that show these features (as described in U.S. Pat. No. 4,374,382 issued to Markowitz et al.) are available in output strip charts.

Our algorithms employ a timing variable which for convenience may be called the mean atrial interval (or MAI or Average Atrial Interval AAI) and represents what the pacing device or "pacemaker" considers the true atrial interval. Our AAI is also designed to converge on the shortest A-A interval (when long-short interval patterns are occurring). This AAI/MAI algorithm is likely to converge on the short AP-AR interval (described above) and thus identify such sequences as atrial tachycardia even in the absence of actual atrial tachycardia. This invention's algorithms can apply to any pacemaker that has false detection of tachycardia or atrial flutter, but one preferred embodiment is found in its application to the MAI in the Thera (TM) Medtronic pacemaker.

Other adjustments can also be made in the modern pacemaker which are described in reference to alternate preferred embodiments herein.

SUMMARY OF THE INVENTION

Alternate methods are available described to prevent false positive atrial tachy detection (meaning detection of non extant tachycardia or flutter). At least one method extends PVARP or PV AB or otherwise causes the pacemaker to avoid sensing or responding to far field R-waves (FFRWs).

Any corrective action to avoid false positive tachy detection that ignores AS events risks missing indications of true tachyarrhythmias. Therefore this invention includes operations to avoid this difficulty as well, mainly by sensing and using possible FFRW events based on screening criteria implemented preferably in software in the IPG. The algorithm first determines if it is possible that 2:1 sensing is occurring and that it would be in the range of suspected atrial tachyarrhythmias (i.e., "the tachy" range). A search routine based on lengthening the PVARP is employed. If atrial tachy is found the device responds, preferably by mode-switching. If sufficient reliability criteria are established, the search may preferably be called off or attenuated.

DETAILED DESCRIPTION OF PREFERRED EMBODIMENTS

First a description of a pacemaker system follows.

Figure 2:
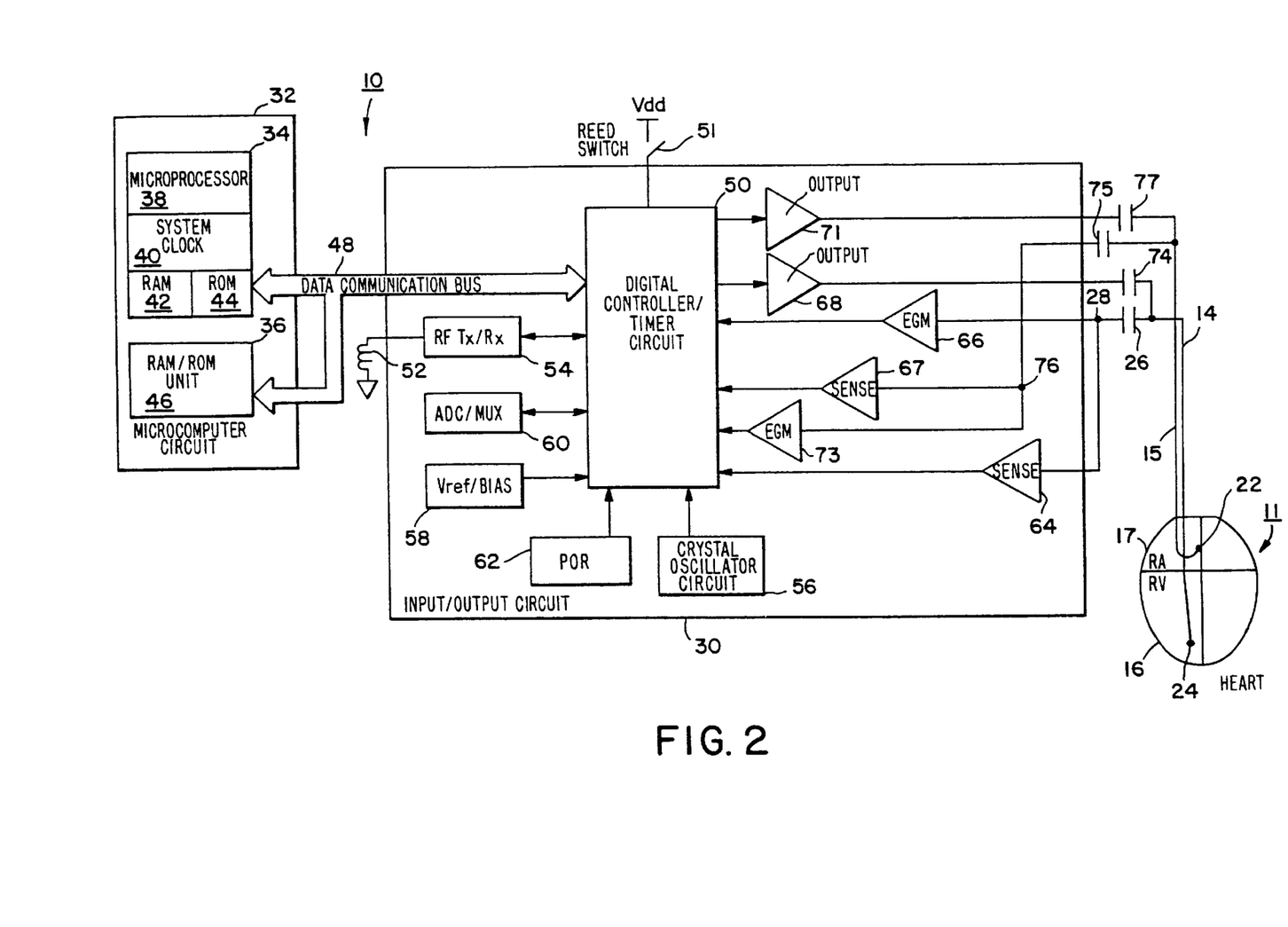
FIGS. 2 is a block diagram of an implantable pulse generator (IPG or "pacemaker") of the type useful with this invention.

FIG. 2 is a block circuit diagram illustrating one possible form of a pacemaker 10 capable of carrying out the present invention. Although the present invention is described in conjunction with a microprocessor-based architecture, it is understood that it could be implemented in other technology such as digital logic-based, custom integrated circuit (IC) architecture, analog circuits, etc., if desired. It is also understood that the present invention may be implemented in cardioverters, defibrillators and the like.

Preferred embodiments would use two leads, 14, 15. Lead 14 includes an electrode 24 located near its distal end positioned within the right ventricle 16. Electrode 24 is coupled by a lead conductor 14 through an input capacitor 26 to the node 28, and to the input/output terminals of an input/output circuit 30. Lead 15 has a distal electrode positioned within the right atrium 17. Electrode 22 is coupled by a lead conductor 15 through an input capacitor 75 to a node 76, and to the input/output terminals of the input/output circuit 30.

Input/Output Circuit 30 contains the operating input and output analog circuits for digital controlling and timing circuits to detect electrical signals derived from the heart, such as the cardiac electrogram (EGM or ECG). It also receives output from sensors (not shown but which may be connected to the leads 14 and 15), and it is the part which applies stimulating pulses to the heart under the control of software-implemented algorithms in a Microcomputer Circuit 32.

Microcomputer Circuit 32 has an On-Board Circuit 34 and an Off-Board Circuit 36. On-Board Circuit 34 includes a microprocessor 38, a system clock 40, and on-board RAM 42 and ROM 44. Off-Board Circuit 36 includes an off-board RAM/ROM Unit 46. Microcomputer Circuit 32 is coupled by Data Communication Bus 48 to a Digital Controller/Timer Circuit 50. Microcomputer Circuit 32 may be fabricated of custom IC devices augmented by standard RAM/ROM components.

It will be understood by those skilled in the art that the electrical components represented in FIG. 2 are powered by an appropriate implantable-grade battery power source (not shown).

An antenna 52 is connected to Input/Output Circuit 30 for purposes of uplink/downlink telemetry through a radio frequency (RF) Transmitter/Receiver Circuit (RF TX/RX) 54. Telemetering both analog and digital data between antenna 52 and an external device, such as an external programmer (not shown), is accomplished in the preferred embodiment by means as substantially described in U.S. Pat. No. 5,127, 404, issued on Jul. 7, 1992, entitled "Telemetry Format for Implantable Medical Device", incorporated herein by reference. A reed switch 51 is connected to Input/Output Circuit 30 to enable patient follow-up via disabling the sense amplifier 146 and enabling telemetry and programming functions, as is known in the art. In this invention, signals indicating whether there is blocked 2:1 sensing that can be stored in memory when the determination is made can be sent to the outside using such telemetry and the circuits just described.

A Crystal Oscillator Circuit 56, typically a 32,768 Hz crystal-controlled oscillator, provides main timing clock signals to Digital Controller/Timer Circuit 50. Most timing periods depend on a clock to turn on or off under program control, and the length of timing is generally established with reference to a number of clock cycles. A Vref/Bias Circuit 58 generates a stable voltage reference and bias currents for the analog circuits of Input/Output Circuit 30. An ADC/Multiplexer Circuit (ADC/MUX) 60 digitizes analog signals and voltages to provide telemetry and a replacement time-indicating or end-of-life function (EOL). A Power-on-Reset Circuit (POR) 62 functions to initialize the pacemaker 10 with programmed values during power-up, and reset the program values to default states upon the detection of a low battery condition or transiently in the presence of certain undesirable conditions such as unacceptably high electromagnetic interference (EMI), for example.

The operating commands for controlling the timing of the pacemaker depicted in FIG. 2 are coupled by bus 48 to Digital Controller/Timer Circuit 50 wherein digital timers set the overall escape interval of the pacemaker, as well as various refractory (PVARP), blanking (PVARB) and other timing windows for controlling the operation of the peripheral components within Input/Output Circuit 50. For this invention these may also include atrial interval values, AV intervals, and so forth.

Digital Controller/Timer Circuit 50 is coupled to sense amplifiers (SENSE) 64 and 67, and to electrogram (EGM) amplifiers 66 and 73 for receiving amplified and processed signals picked up from electrode 24 through lead 14 and capacitor 26, and for receiving amplified and processed signals picked up from electrode 22 through lead 15 and capacitor 75, representative of the electrical activity of the patient's ventricle 16 and atrium 17, respectively. Similarly, SENSE amplifiers 64 and 67 produce sense event signals for re-setting the escape interval timer within Circuit 50. The electrogram signal developed by EGM amplifier 66 is used in those occasions when the implanted device is being interrogated by the external programmer/transceiver (not shown) in order to transmit by uplink telemetry a representation of the analog electrogram of the patient's electrical heart activity as described in U.S. Pat. No. 4,556,063, issued to Thompson et al., entitled "Telemetry System for a Medical Device", incorporated herein by reference.

Output pulse generators 68 and 71 provide the pacing stimuli to the patient's heart 11 through output capacitors 74 and 77 and leads 14 and 15 in response to paced trigger signals developed by Digital Controller/Timer Circuit 50 each time the escape interval times out, or an externally transmitted pacing command has been received, or in response to other stored commands as is well known in the pacing art.

In a preferred embodiment of the present invention, pacemaker 10 is capable of operating in various non-rate-responsive modes which include DDD, DDI, VVI, VOO and VVT, as well as corresponding rate-responsive modes of DDDR, DDIR, VVIR, VOOR and VVTR. Further, pacemaker 10 can be programmably configured to operate such that it varies its rate only in response to one selected sensor output, or in response to both sensor outputs, if desired. Many other features and functions of pacemakers may be incorporated without going beyond the scope of this invention.

Some background information about marker channels and how pacemakers keep information regarding A-A intervals is also required.

Figure 1:
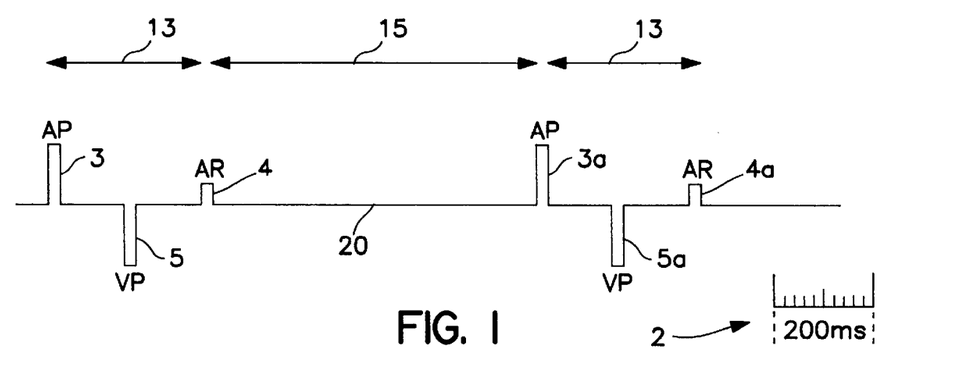
FIG. 1 is a marker channel diagram providing an example of a timing scenario which can cause false positive tachy detection and mode switching.

Referring now to FIG. 1, although a number of algorithms could be used to determine the average atrial interval, the ones we use tend toward convergence on the shortest atrial interval value in a repeating sequence. (This can be recognized by examining the AAI algorithm discussed below.) This convergence on the shortest time AA interval is how mode switching is generally triggered. (We assume this is the "true" A-A value and call this updated atrial interval value either the Average Atrial Interval (AAI) or Mean Atrial Interval (MAI) for convenience.) These A-A interval time values tend to be significantly shorter than atrial pace to atrial pace intervals as can be easily seen in FIG. 1. Here a marker channel diagram 20 is illustrated with atrial pace indicators 3/3a, atrial refractory event indicators 4/4a, and ventricular pace indicators 5/5a. The arrows 13 (for AP-AR intervals) and 15 (for AR-AP intervals) indicate the likely differences in timing between atrial to atrial events for this patient. For size reference, indicator scale 2 is included on the diagram of FIG. 1.

Figure 3:
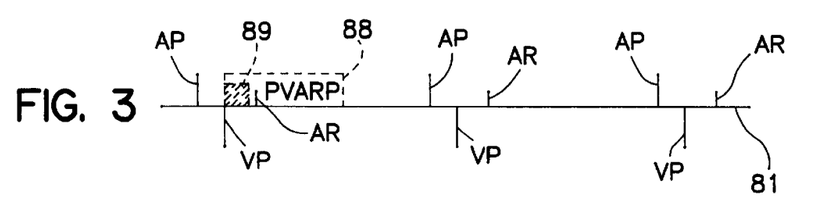
FIGS. 3–5 are marker channel diagrams.
Figure 4:
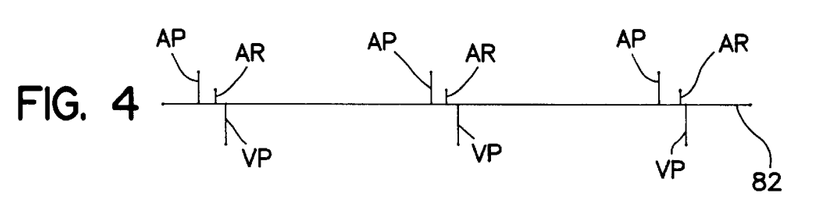

FIGS. 3 and 4 illustrate cases where false tachy detection could occur, as shown in these marker channel diagrams (illustrated as lines or graphs 81 and 82). The atrial pace, atrial refractory, and ventricular pace events are simply indicated with AP, AR, and VP, respectively. In FIG. 3 a sensed event in a post ventricular atrial refractory period (PVARP 88) (shown here as AR) may be due either to far field R-waves (FFRWs), T-wave sensing, retrograde conduction, skeletal muscle activity artifacts, or any other sense occurring during PVARP, or false atrial sensing due to polarization after a pacing pulse. (For heuristic purposes and reference a PVAB period 89 is also shown within the PVARP 88 in FIG. 3.) In a second case (FIG. 4), a sense during the Atrio Ventricular (AV) interval is shown. This may be due to ventricular fusion pacing, loss of atrial capture, junctional rhythm, or any other atrial sense during the AV interval which can fool the tachy detection algorithm by suggesting that the true atrial interval is very short.

Far field R-wave sensing may occur in cases other than an AP-AR-AP rhythm. It is also possible to get a far field R-wave after a sinus rhythm, producing an AS-VP-AR marker channel series. While in general it may be assumed that the marker channel diagram of FIG. 3 has appropriately labeled marker signals, these may be incorrect. For example, a far field R-wave or other signal may appear to be something other than it seems. If that is the case, the marker channel generator will label it incorrectly, indicating that the pacemaker may respond incorrectly.

In other pulse generators, there may be no marker channel reference but the device may nonetheless misinterpret signals. The marker channel is used in this description because it is much more easily read than strip charts and because it indicates how the pacemaker is interpreting the sensed signals it is receiving from the heart and its environment.

Valuation of the "AAI" or "MAI"(A Variable Stored and Updated by the Pacemaker)

The current value of the Average Atrial Interval is normally adjusted by a microcomputer circuit as illustrated in FIG. 2 continuously following every atrial interval which ends in an intrinsic (atrial non-paced) event and those intervals between two atrial paced events.

There are numerous ways to adjust the AAI. These fall into three categories. 1) Ignoring certain individual cardiac sense events that occur during blanking periods, 2) ignoring other individual events that do not qualify because of the type of signal or the timing of the signal received, and 3) a set of methods through manipulation of the algorithm itself used to determine and update AAI. While many functions of a pacemaker may be dependent upon the calculation used to evaluate such an AAI variable, its clearest indication is in determining whether or not there is a tachycardia present. In general, AAI=F(N), that is the value called the Average Atrial Interval is a function of "N",. where N is a continuously updated value dependent on determination of atrial sensed events and the timing between one atrial sensed event and the next.

Thus the value of AAI can be shifted by ignoring certain atrial events that occur generally too close to a previous event, are of too small an amplitude, or occur too long after a previous event. On the occurrence of a valid A to A event interval, the value of that time period between the occurrence of first event and the second event is used to increase or decrease the value of AAI. This can be done directly or indirectly and various algorithmic filters and limitations may be put on this additive or subtractive function as will occur to the reader of ordinary skill in these arts.

A primary concern of this patent is to determine a value for the appropriate A to A interval in order to make a judgment about whether or not a tachyarrhythmic event is occurring. For example, in a sinus tracking situation, where every atrial event is a sensed (intrinsic) event, each A-A interval would be used in adjusting the AAI. In a competitive pacing situation, where atrial pacing is closely coupled to intrinsic atrial activity, the Refractory Sense-Pace interval should not be used as it may not actually reflect underlying intrinsic activity.

Depending on the sophistication of the pacemaker or implanted pulse generating device, the internal recordkeeping of the AAI may be maintained in several places and if desired several different values can be used, one for each particular purpose.

In the presently preferred embodiment, updating the AAI is a "biased delta" operation. Each adjustment modifies the AAI by a fixed amount. If the measured A-A interval used for an update of the AAI is smaller than or equal to the current AAI, the AAI is reduced by a fixed amount, called "DELTADEC". Likewise, if the A-A interval used for an update of the AAI is larger than the current AAI, the AAI is increased by a different fixed amount, "DELTAINC". DELTADEC and DELTAINC are included among the programmable values that may be selected and modified or manipulated by a physician. Such change of values is accomplished using the pulse generator's telemetry programming facilities, to modify certain memory locations in the device. Such telemetry and communication is a well-known practice in the art.

For any given update, the AAI used in the preferred embodiment can never change by more than the DELTADEC or DELTAINC values. In the presently preferred implementation of the invention, DELTADEC is larger than DELTAINC. This results in a rate-smoothing pattern that tracks rapidly increasing atrial rates faster than decreasing atrial rates.

One result of the step-wise incrementing and decrementing of the AAI is that it is possible for the AAI to overshoot the intrinsic atrial rate. For example, if it is assumed (1) that a current AAI value is 600-mSec (milliseconds); (2) that the programmed DELTADEC value is 24-mSec; (3) that the programmed DELTAINC value is 8-mSec; (3) that an atrial sense occurs 550-mSec following a prior atrial sense (i.e., a measured atrial interval of 550-mSec). Then this will result in an updated AAI value of 576-mSec (600–24). If (4), the next intrinsic atrial event occurs 560-mSec following the one for which the AAI was updated to 576-mSec, the next AAI update would again entail decrementing the current AAI by 24-mSec. This adjustment, however, would result in an AAI of 552, slightly smaller than the intrinsic A-A interval (560-mSec) just measured. If the next intrinsic atrial event is in 560-mSec from the last one, DELTA INC. will be added to 552 yielding a new AAI of 560-mSec.

Adjusting the AAI/MAI to Exclude Certain Sequences

Figure 5:
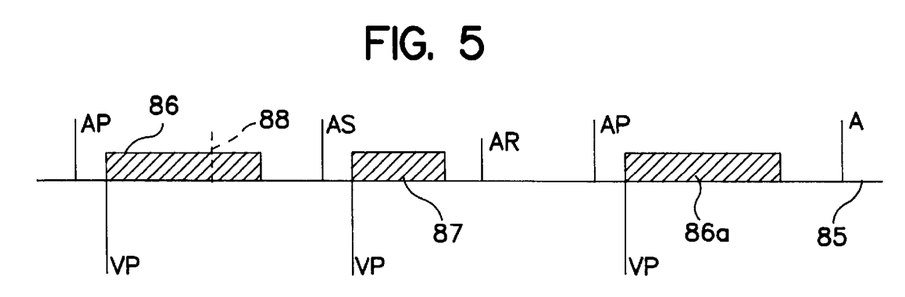

FIG. 5 is a marker channel diagram 85, illustrating two PVAB's (post ventricular atrial blanking periods) as numerals 86 and 87 and also illustrating a blanked atrial refractory sense 88. Starting at the left, the AP-AS (blanked at 88)—AR sequence is interpreted as an A-A interval measured from AP to AS, since the FFRW-type signal at 88 is ignored. Thus, in the case of a long PVAB (Post Ventricular Atrial Blanking period) like PVAB 86, the next marker channel atrial event is further out and a long A-A interval is used to update the MAI. Where the PVAB is shortened because it occurs after an atrial sense (not a paced) event as in PVAB 87, the AR or FFRW event is the next considered event by the tachy detection algorithm. In other words, the AS-AR interval will shorten the MAI/AAI (because it's a short time period), and if short enough the MAI size will indicate a tachy condition, and cause a mode switch. In this way the AAI/MAI is automatically adjusted by the changed length of the PVAB. In a preferred embodiment there are two possible PVAB lengths, one near 200 msecs and the short one around 150 msecs.

FFRW Sensing

If the device can sense FFRW's an alternative to avoid false tachy detection is available by selectively removing only some of the FFRW's from consideration in determining the size of the atrial (A-A) interval. To do this we assume that the atrial lead sense amplifier is left "on" during the time period in the PVARP that does not overlap the PVAB. By determining whether the particular sensed event found during this "sensor-on" time period should be counted or not, it can be used to adjust the pacemaker's representation of value for the A-A interval, the MAI/AAI, or "true A-A interval."

SOLUTION TO OVERLONG PVAB CAUSING LOSS OF VALID TACHY DETECTION

Figure 6:
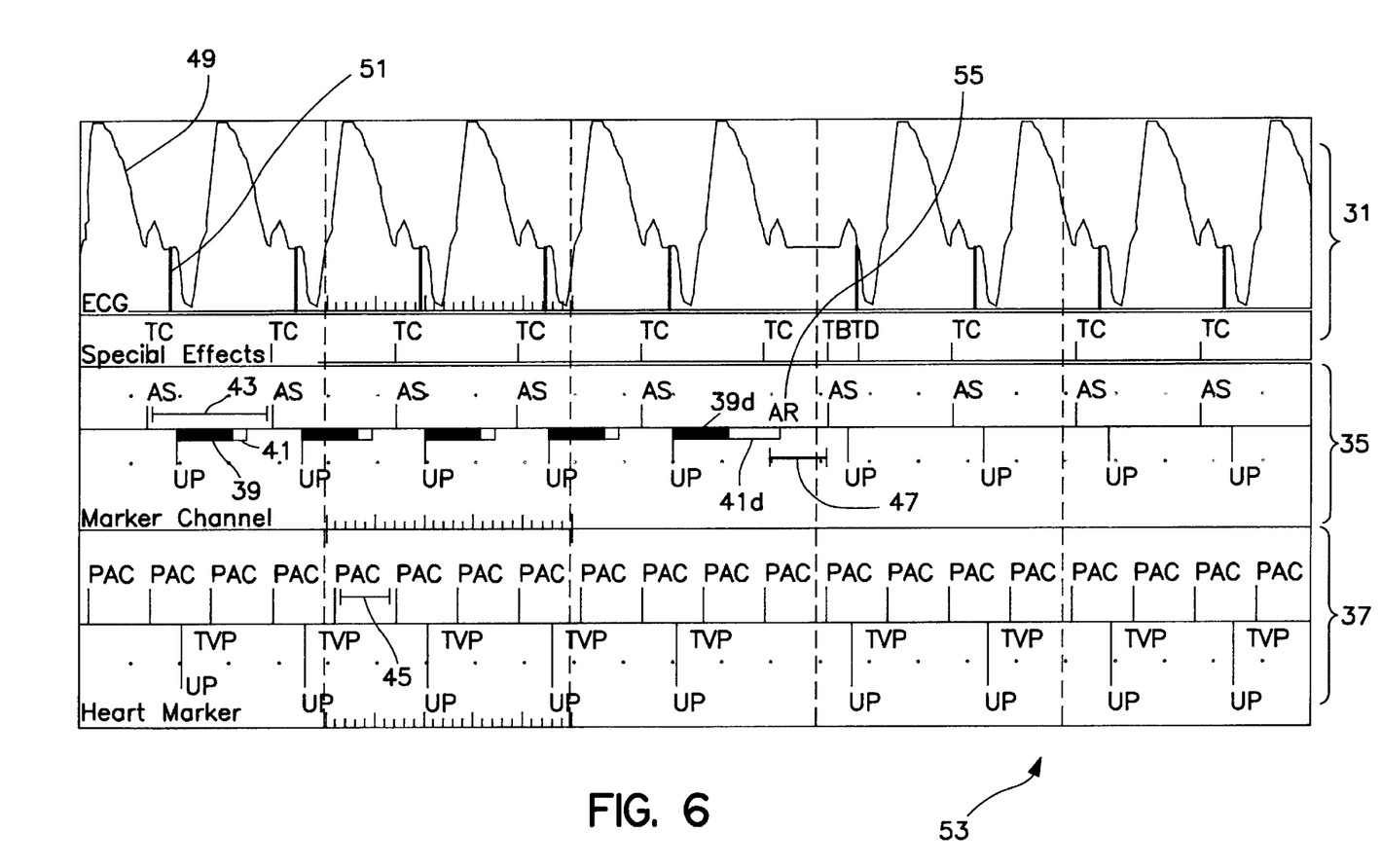
FIG. 6 and 7 are combined ECG and marker channel graphs.

Because a tachy arrhythmia cannot be detected in the atrium while the atrial sense amplifier is turned off, if the PVAB is too long it will mask indicators of real tachycardia. A common manifestation is "2:1 sensing", i.e., only every atrial event is sensed. We call this "blocked 2:1 sensing". An example can be seen in FIG. 6 in which a combined 53 marker channel 31 and ECG chart 35 are shown, together with a heuristic "Heart Marker" chart 37, as can be constructed in simulation. The PACs indicate temporal location of atrial contractions of the simulated heart, and the VPs represent ventricular pacing events. PVABs are the dark boxes(39–39d) and the remainder of the PVARP is indicated with numerals 41–41d. the spacer 45 on the marker channel chart 35 indicates the size of the MAI or its equivalent, based on the putative ECG in chart 31. The actual size atrial interval is illustrated as spacer 47. Note that it is the equivalent size to the space between each PAC in chart 37. Manipulation of the PVAB and PVARP as described hereinbelow will yield the AR signal in the marker channel at 55. Otherwise, because of an atrial blanking period as long as that indicated at numeral 39, these signals will not be seen by the IPG, because the atrial sense amplifier will be "blanked" or turned off.

Figure 8:
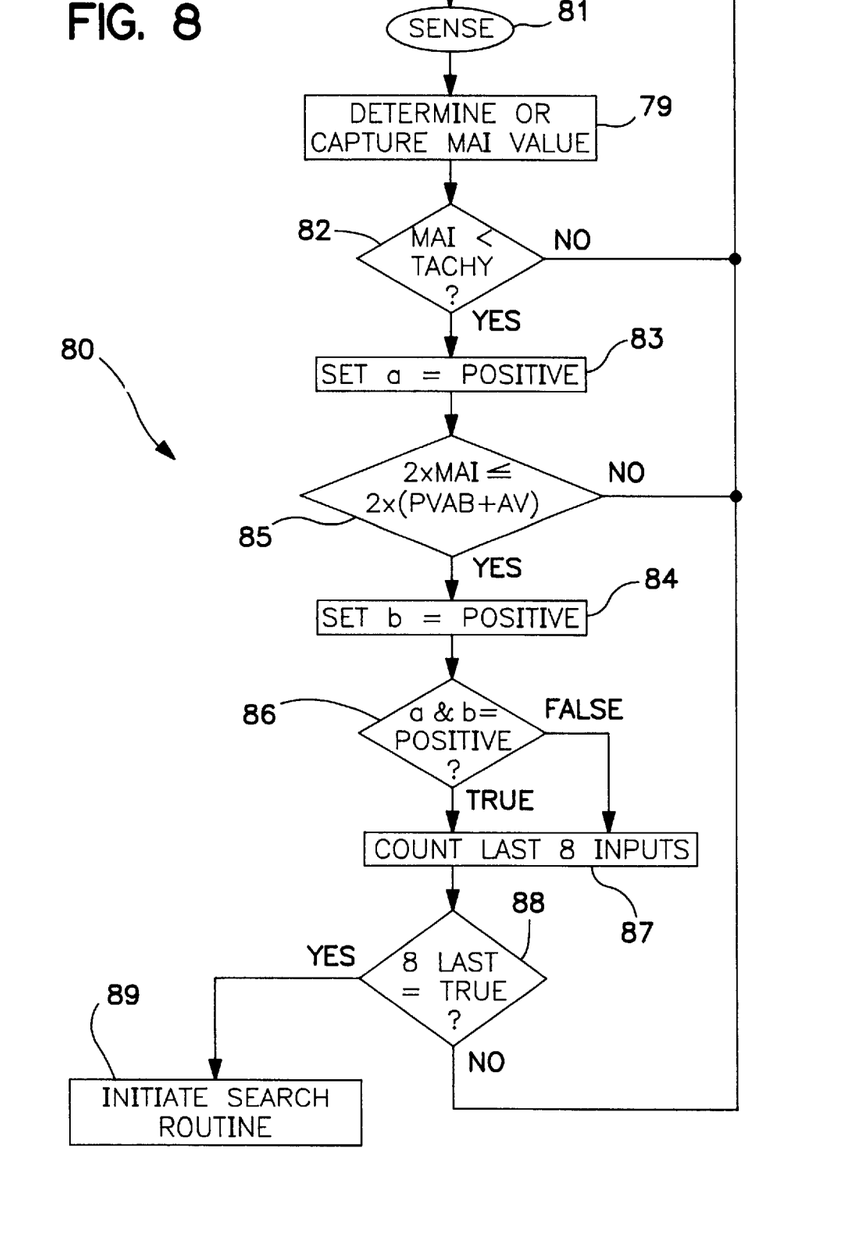
FIGS. 8 and 9 are flow charts.

This solution determines whether it is possible that the PVAB is too long and masking a 2:1 sensing condition in which only every other atrial event is sensed. FIG. 8 is a flow chart that illustrates when the IPG is to perform a search in accord with the preferred embodiment. It starts by looking at the value of the instantaneous A-A interval, then determining if this instantaneous value meets the two rules described below in steps 82 and 85. If both these rules are met (steps 83 and 84) the process algorithm increases a counter until it shows that both rules have been met 8 times in a sequence. Until that becomes true, it waits for the next sense in the atrium 81 and restarts itself, but maintains the counter. Changing the size or the demand for a full counter are just some alternatives for determining reliability, and other criteria could be used. If experience shows that once through the algorithm 80 is sufficient to start a search in a particular patient, that may be done also. The algorithm 80 also restarts itself any time either of the rules are not met for a given atrial sense. It is applied using two rules:

RULE 1: If the A-A interval<=2 times the sum of the AV interval plus the PVAB length, then it is possible that there is 2:1 sensing, otherwise it's not.

RULE 2: If Rule 1 is satisfied and ½ the A-A interval is less than a programmed "tachy interval" then such possible 2:1 sensing, if it exists, is defined as pathological; otherwise it is not.

(It should be recognized that these rules may be applied in either order.)

The preferred embodiment pacemaker counts the number of beats that possible 2:1 sensing is true for eight consecutive cardiac cycles. If all eight don't satisfy the rule, it starts again.

Figure 7:
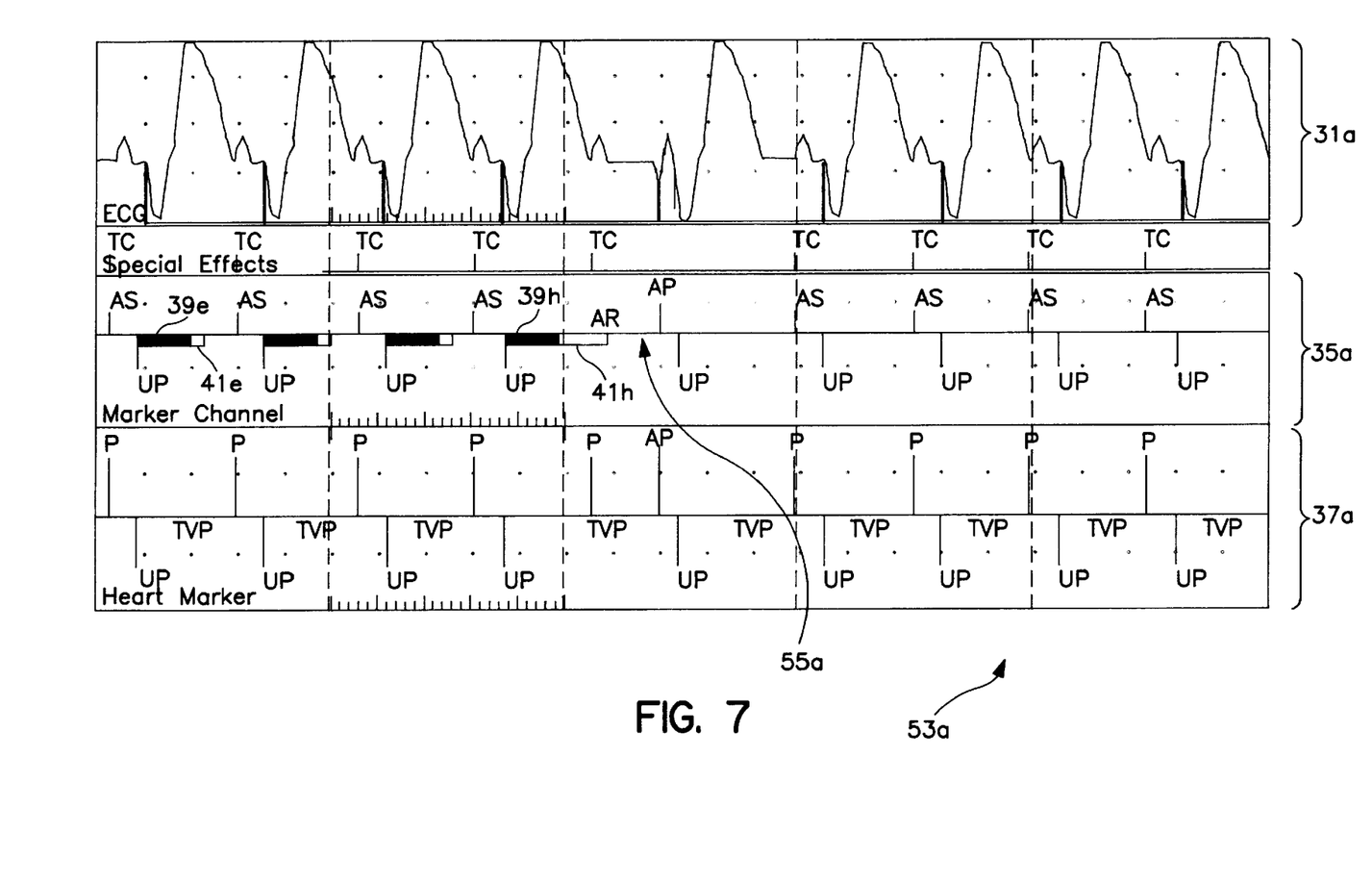

Once eight consecutive cycles pass where Rule 1 and 2 are satisfied, the pacemaker modifies its timing parameters to check for actual 2:1 sensing. To do so it performs what we call "search cycles" during which three parameters should be changed as follows. The PVARP is adjusted (longer) so as to force the next expected sensed atrial event into the PVARP. The PVAB may also be adjusted to be shorter. The subsequent AV intervals are shortened as a precaution to assure minimum drop in ventricular rate during continued atrial tracking. Also, because the time of the expected tachy sense is one and one half times the measured A-A interval, the escape interval should be adjusted to deliver an atrial pace just after the expected tachy sense. The application of this atrial pace based on the time-out of an escape interval can be seen in FIG. 7, at 55. This may increase or decrease the escape interval if desired.

Figure 9:
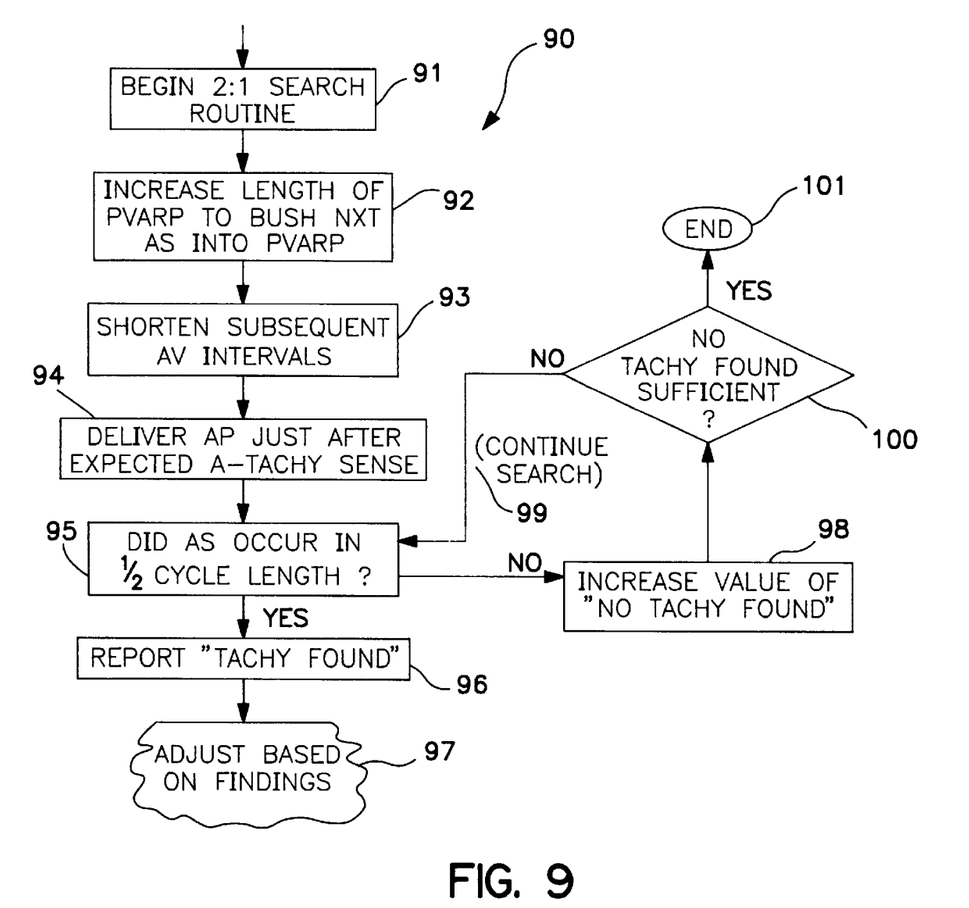

The search routine is set out in FIG. 9 as algorithm 90, starting with an initiation step 91, causing the length of PVARP to be increased 92 and the subsequent AV intervals to be shortened 93. (An Atrial Pace is to be delivered just after any expected tachy sense time when such a sense does not occur, 94 to be sure the heart pumps in synchrony or near it.) After step 94, the algorithm 90 detects or determines whether an AS occurred at or near ½ the assumed cycle length after AR. If not, the reliability of the determination that no tachy has occurred is increased 98, and when that value is sufficient as determined in step 100, the program goes to step 101, ending this search and allowing the need for searching in the future to be attenuated or eliminated if desired.

If an AS did occur when expected (after AR), after step 95 the algorithm reports the same to the responding program in the IPG which can adjust further use of this search program as well as order response to the perceived tachy condition.

Thus, performing this search cycle will lead to two mutually exclusive possibilities:

A. If an atrial tachycardia exists an atrial event will occur after the event pushed into PVARP at near ½ the sensed A-A interval, or B. an atrial pace will be the next atrial event after the AR.

In the preferred embodiment, if possibility B occurs (meaning that no tachy intrinsic pulse occurred when one would be expected if there were 2:1 sensing), the search cycle is repeated a short time ( preferably several cardiac cycles) later until an adequate number of repeated B events provide assurance that there is no tachycardia. Future searches can be delayed a programmable time, which can continue to grow (if desired to save battery power) for so long as no tachy pulses are found.

To implement this solution, one may optionally add these rules and an initiation of search sequence to the algorithm that lengthens or shortens PVAB based on whether it is an atrial pace or sensed event that has occurred.

Other uses for this method and device may occur to the reader but the scope of this invention is limited only by the following claims:

If desired, such attenuation can finally result in turning off the use of the search altogether.

What is claimed is:

1. A method for determining if a long Post Ventricular Atrial Blanking period (PVAB) is blocking the sensing of every other atrial beat which may occur in a heart atrium (called "blocked 2:1 sensing") for use by a device which keeps data on time intervals between cardiac events for a living heart, such data at least including Atrial beat to Atrial beat time periods (A-A intervals), and Atrial beat to Ventricular beat time period (AV intervals) as well as said PVAB, comprising the steps:

sensing in the atrium to determine A-A intervals, determining (a) whether there is possible blocked 2:1 sensing by determining if said A-A interval is less than or equal to two times the sum of the AV interval plus the PVAB, determining (b) whether one-half the A-A interval is less than a tachy interval, and if (a) and (b) are true, then adjusting device parameters to accomplish a search cycle for determining whether in fact tachycardia is occurring during said possible blocked 2:1 sensing.

2. A method as set forth in claim 1 further comprising:

the step of determining whether (a) and (b) are true for a predetermined period to establish reliability of whether there is possible blocked 2:1 sensing before said step of adjusting said parameters to accomplish a search cycle step.

3. A method of searching for blocked 2:1 atrial sensing in an Implantable Pulse Generator(IPG) so as to enable a determination of whether atrial tachycardia is occurring at a rate approximately two times that of an expected cardiac cycle length, comprising:

adjusting IPG parameters to accomplish a search cycle by lengthening a Post Ventricular Atrial Refractory Period (PVARP) so as to change the time for sensing atrial events such that a time window to expose a blocked 2:1 atrial sense is opened, and sensing during that time window for said previously blocked 2:1 sense, and if said previously blocked 2:1 sense is found in said time window, then generating a tachy atrial sense occurred signal.

4. A method as set forth in claim 3 for use by a device which keeps data on time intervals between cardiac events for a living heart, such data at least including Atrial beat to Ventricular beat time period (AV intervals) and further comprising:

further adjusting IPG parameters by shortening AV intervals subsequent to such lengthened PVARPs.

5. A method as set forth in claim 3 or 4 and further comprising:

determining if an Atrial Refractory event (AR) is sensed to have occurred at a time near ½ an expected cardiac cycle length.

6. A method as set forth in claim 3 and further comprising:

causing an atrial pace to occur just after a tachy atrial sense is expected if said atrial tachy sense occurred signal is generated.

7. A method of searching for blocked 2:1 atrial sensing in an Implantable Pulse Generator(IPG) so as to enable a determination of whether atrial tachycardia is occurring at a rate approximately two times that of an expected cardiac cycle length, comprising:

adjusting IPG parameters to accomplish a search cycle by shortening a Post Ventricular Atrial Blanking Period (PVAB) so as to change the time for sensing atrial events such that a time window to expose a blocked 2:1 atrial sense is opened, and sensing during that time window for said previously blocked 2:1 sense, and if said previously blocked 2:1 sense is found in said time window, then generating a tachy atrial sense occurred signal.

8. A method as set forth in claim 7 and further comprising:

further adjusting pacemaker parameters by shortening AV intervals subsequent to lengthened PVARPs.

9. A method as set forth in claim 7 or 8 and further comprising:

determining if an Atrial Refractory event (AR) is sensed to have occurred at a time near ½ an expected cardiac cycle length.

10. A method as set forth in claim 7 and further comprising:

causing an atrial pace to occur just after a tachy atrial sense is expected if said tachy atrial sense occurred signal is generated.

11. A method for determining whether blocked 2:1 sensing is occurring as set forth in claims 3 or 7 and further comprising recording signals in memory means for subsequent telemetry to outside the IPG an indication that blocked 2:1 sensing has occurred.

12. A method for determining whether blocked 2:1 sensing is occurring as set forth in claims 3 or 7 and further comprising performing the method of claims 3 or 7 at a frequency, and attenuating the frequency of employing the method of searching of claims 3 or 7 in a manner corresponding to the number of times blocked 2:1 sensing is not found for each time when said method of searching is employed.

13. A method as set forth in claim 12 wherein said attenuation ends in turning off the search.

* * * * *